US012622964B2

(12) United States Patent
Danielli et al.

(10) Patent No.: US 12,622,964 B2
(45) Date of Patent: May 12, 2026

(54) MODULAR PHAGE VECTOR PLATFORM FOR SONODYNAMIC THERAPY

(71) Applicant: ALMA MATER STUDIORUM—Universita' di Bologna, Bologna (IT)

(72) Inventors: Alberto Danielli, S. Lazzaro di Savena (IT); Matteo Calvaresi, Bologna (IT); Matteo Di Giosia, Bologna (IT); Andrea Cantelli, Bologna (IT); Francesco Starinieri, Pescara (IT); Michela Nigro, Dozza (IT); Edoardo Sarti, Prato (IT)

(73) Assignee: ALMA MATER STUDIORUM—Universita' di Bologna, Bologna (IT)

( * ) Notice: Subject to any disclaimer, the term of this patent is extended or adjusted under 35 U.S.C. 154(b) by 1077 days.

(21) Appl. No.: 17/596,746

(22) PCT Filed: Jun. 26, 2020

(86) PCT No.: PCT/IB2020/056058
§ 371 (c)(1),
(2) Date: Dec. 17, 2021

(87) PCT Pub. No.: WO2020/261199
PCT Pub. Date: Dec. 30, 2020

(65) Prior Publication Data
US 2022/0296710 A1 Sep. 22, 2022

(30) Foreign Application Priority Data

Jun. 26, 2019 (IT) ........................ 102019000010131
Nov. 26, 2019 (IT) ........................ 102019000022200

(51) Int. Cl.
| | |
|---|---|
| A61K 35/76 | (2015.01) |
| A61K 41/00 | (2020.01) |
| A61K 47/69 | (2017.01) |
| A61P 31/04 | (2006.01) |
| A61P 35/00 | (2006.01) |
| C12N 7/00 | (2006.01) |

(52) U.S. Cl.
CPC .......... *A61K 41/0033* (2013.01); *A61K 35/76* (2013.01); *A61K 47/6901* (2017.08); *A61P 31/04* (2018.01); *A61P 35/00* (2018.01); *C12N 7/00* (2013.01); *C12N 2795/14121* (2013.01); *C12N 2795/14132* (2013.01)

(58) Field of Classification Search
None
See application file for complete search history.

(56) References Cited

PUBLICATIONS

Stephanopoulos, N., et al: "Dual-Surface Modified Virus Capsids for Targeted Delivery of Photodynamic Agents to Cancer Cells", ACS Nano, vol. 4, No. 10, Oct. 26, 2010 (Oct. 26, 2010), pp. 6014-6020, XP055680985, US ISSN: 1936-0851, DOI: 10.1021/nn1014769 (Year: 2010).*
Li, K., et al: "Chemical Modification of Mi3 Bacteriophage and Its Application in Cancer Cell Imaging", Bioconjugate Chemistry, vol. 21, No. 7, Jul. 21, 2010 (Jul. 21, 2010), pp. 1369-1377, XP055056043, ISSN: 1043-1802, DOL 10.1021/bc900405q (Year: 2010).*
Costley, D., Mc Ewan, C., Fowley, C., McHale, A. P., Atchison, J., Nomikou, N., & Callan, J. F. (2015). Treating cancer with sonodynamic therapy: A review. International Journal of Hyperthermia, 31(2), 107-117. https://doi.org/10.3109/02656736.2014.992484 (Year: 2015).*
Serpe, L., Giuntini, F., Sonodynamic antimicrobial chemotherapy: First steps towards a sound approach for microbe inactivation, Journal of Photochemistry and Photobiology B: Biology, vol. 150, 2015, pp. 44-49, ISSN 1011-1344, https://doi.org/10.1016/j.jphotobiol.2015.05.012. (Year: 2015).*
Inui, T et al., Case Report: A Breast Cancer Patient Treated with GcMAF, Sonodynamic Therapy and Hormone Therapy, 2014, International Institute of Anticancer Research, Anticancer Research, vol. 38, pp. 4589-4593, (Year: 2014).*
Embleton M.L., et al., "Development of a novel targeting system for lethal photosensitization of antibiotic-resistant strains of Staphylococcus aureus", Antimicrobial Agents and Chemotherapy, vol. 49, No. 9, Sep. 1, 2005, pp. 3690-3696.
Li K, et al., "Chemical modificaiton of M13 bacteriophage and its application in cancer cell imaging", Bioconjugate Chemistry, vol. 21, No. 7, Jul. 21, 2010, pp. 1369-1377.
Ma J. et al., "Virus-based nanocarriers for drug delivery", Advanced Drug Delivery Reviews, vol. 64, No. 9, Jan. 12, 2012, pp. 811-825.
Rhee J-K et al., "Glycan-targeted virus-like nanoparticles for photodynamic therapy", Biomacromelecules, vol. 13, No. 8, Aug. 13, 2012, pp. 2333-2338.
Search Report and Written Opinion of PCT/IB2020/056058 of Oct. 1, 2020.
Stephanopoulos N. et al., "Dual-surface modified virus capsids for targeted delivery of photodynamic agents to cancer cells", ACS Nano, vol. 4, No. 10, Oct. 26, 2010, pp. 6014-6020.
Wan G-Y et al., "Recent advances of sonodynamic therapy in cancer treatment", Cancer Biology & Medicine, vol. 13, No. 3, Jan. 1, 2016, pp. 325-338.

* cited by examiner

*Primary Examiner* — Anna Skibinsky
*Assistant Examiner* — Catherine L McCormick
(74) *Attorney, Agent, or Firm* — Silvia Salvadori, P.C.; Silvia Salvadori

(57) ABSTRACT

The present invention relates to a phage or a composition that comprises it, wherein said phage expresses at least one specific recognition element and is furthermore conjugated with at least 300 molecules of a sonosensitiser. The invention further relates to the use of said phage in a sonodynamic therapy.

16 Claims, 5 Drawing Sheets

MODULAR PHAGE VECTOR PLATFORM FOR SONODYNAMIC THERAPY

This application is a U.S. national stage of PCT/IB2020/056058 filed on 26 Jun. 20202 which claims priority to and the benefit of Italian patent application No. 102019000010131 filed on 26 Jun. 2019, and claims priority to and the benefit of Italian patent application No. 102019000022200 filed on 26 Nov. 2019, the content of which are all incorporated herein by reference in their entireties.

FIELD OF THE INVENTION

The present invention relates to a phage or a composition comprising it, wherein said phage expresses at least one specific recognition element and is furthermore conjugated with at least 300 molecules of a sonosensitiser. In addition, the invention relates to the use of said phage in a sonodynamic therapy.

PRIOR ART

Bacteriophages (phages) are ubiquitous viruses which infect bacteria while being inactive against eukaryotic cells. Phages are biocompatible, uniform in size and in morphology, and relatively stable at high temperatures, in a broad pH range. For this reason, phages, such as, for example, the M13 phage, have been receiving growing attention as an ordered protein platform for the assembly of functional molecules and nanostructured materials. Directing molecules and therapeutic effectors can be easily exposed or conjugated on their surface. The M13 phage can be directed at virtually any type of cell through the exposure of specific peptides or antibodies. Furthermore, its excellent safety profile makes it highly suitable for in vivo applications.

US2007/0020241 describes bacteriophages conjugated to photosensitisers and said conjugate has shown to be effective in killing bacteria when irradiated with light of suitable wavelength.

Li, K., et al., in Chemical Modification of M13 Bacteriophage and Its Application in Cancer Cell Imaging. Bioconjug. Chem. (2010) 21, 1369-1377, describe the conjugation of photoreactive molecules to the M13 phage, wherein a quenching effect is noted when more than 500 molecules are conjugated to the phage.

Progress beyond phototherapy has been achieved with sonodynamic therapy (SDT), an approach that involves a combination of low-intensity ultrasound and specialised chemical agents known as sonosensitisers. Activation of the sensitiser by ultrasound generates reactive oxygen species (ROS) responsible for cytotoxicity. Being able to penetrate more deeply into tissues than light irradiation, ultrasound also enables treatment in deep regions. By way of example, ultrasound can be focused in a region of a tumour in order to activate a sonosensitiser, thus offering the possibility of striking tumours in a targeted manner.

The available sonosensitisers include sonosensitisers based on porphyrins or on xanthens. Use has also been made of small molecules, including curcumin, indocyanine green (ICG), acridine orange, and hypocrellin B. One of the limits most strongly perceived with SDT is tied to the high ultrasonic powers that need to be deployed in order to obtain an effective activation of sonosensitisers.

It is an object of the present invention to provide a system for an effective SDT.

SUMMARY OF THE INVENTION

A first aspect of the present invention relates to a phage conjugated with at least one sonosensitiser. The phage preferably expresses at least one specific recognition element adapted to favour binding of the phage with target cells, such as, for example, bacterial cells or tumour cells.

A second aspect of the present invention relates to a composition comprising the phage and excipients and/or additional substances and/or pharmaceutically accepted carriers.

A third aspect of the present invention relates to the phage or to the composition that comprises it for use as a medicament, preferably in a sonodynamic therapy (SDT).

A fourth aspect of the present invention relates to the phage or to the composition that comprises it for use in the treatment or follow-up of a tumour, preferably a malignant tumour.

A further aspect of the present invention relates to the phage or to the composition that comprises it for use in the treatment or prevention of an infection selected from a bacterial, viral or fungal infection, preferably a bacterial infection.

A further aspect of the present invention relates to a method for the treatment or follow-up of a tumour, preferably a malignant tumour, or for the treatment or prevention of an infection. Said method comprises at least a step of administering an effective amount of a phage, or of a composition that comprises it as described in detail above, to an individual affected by a tumour or an infection.

DEFINITIONS

Figure 1:
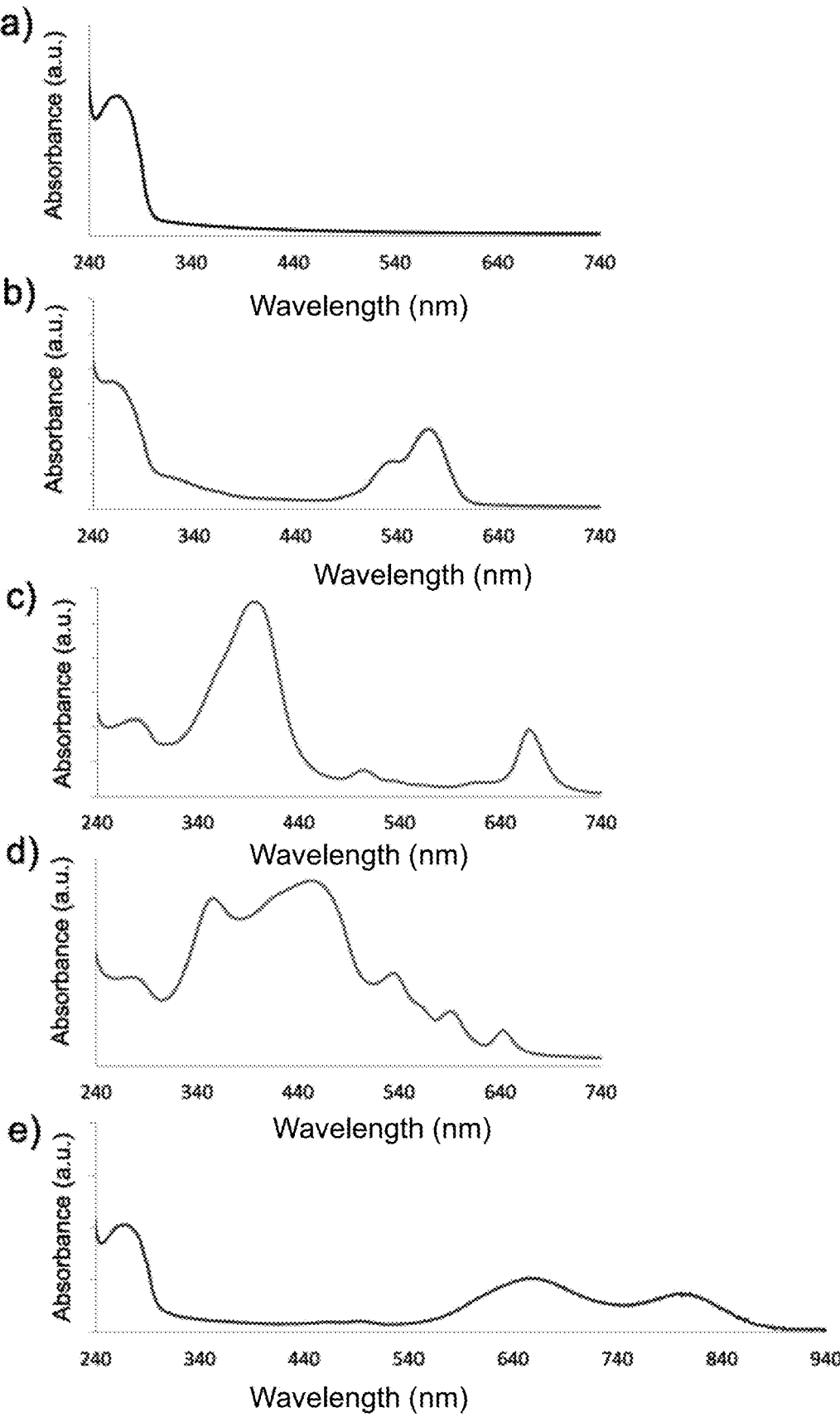
FIG. 1 shows the absorbance spectra of the a) wild-type M13 phage and conjugates b) phage-Rose Bengal, c) phage-Chlorin e6, d) phage Protoporphyrin IX, and e) phage-Cyanine IR-806.

In the context of the present invention, the term "bacteriophage" or "phage" means a virus that only parasitises bacteria, whose destruction it can bring about.

In the context of the present invention, the term "sonosensitiser" means a molecule capable of generating reactive oxygen species (ROS) following irradiation with ultrasound.

In the context of the present invention, the term "sonodynamic therapy (SDT)" means a non-invasive therapy that envisages the combined use of ultrasound and sonosensitisers, which can generate reactive oxygen species (ROS).

In the context of the present invention the term "specific recognition element" means an element capable of recognising, in a specific and selective manner, a second element expressed by a cell or a virus.

DETAILED DESCRIPTION OF THE INVENTION

A first aspect of the present invention relates to a phage conjugated with at least one sonosensitiser. In one embodiment, said phage is preferably selected from: M13 phage, fd phage, Ff phage, T4 and MS2 phage. The phage is preferably the M13 phage.

The sonosensitiser is preferably selected from: Bacteriochlorin, Phthalocyanines, Pheophorbide A and B, Bacteriopheophorbide, Naphthalocyanine, BODIPY stains, Anthracycline, Tetracycline, Fluoroquinolones, Phenothiazine, Perylene, Perylenequinone, Curcumin, Quinones, Anthraquinones, Fullerenes, Endohedral Metallofullerenes, Acridines, Isoquinole alkaloids, Xanthenes, Porphyrins, Chlorins and Cyanine.

In one embodiment, the sonosensitiser is selected from: a xanthen, preferably rose bengal, eosin, erythrosin B, fluorescein and rhodamine; a porphyirin, preferably protoporphyirin IX, hematoporphyirin, porfimer sodium and ATX-70; a chlorin, preferably chlorin e6, temoporfin and verteporfin; a cyanine, preferably cyanine IR-806, indocyanine green and cyanine IR-780. The sonosensitiser is preferably selected from Rose Bengal, Chlorin e6, Protoporphyirin IX and Cyanine IR-806 and combinations thereof.

In one embodiment, the phage is conjugated with at least 300 molecules of a sonosensitiser, preferably with at least 400 molecules, more preferably with at least 500 molecules, even more preferably with at least 700 molecules of a sonosensitiser.

The conjugation takes place with methods known to the person skilled in the art; it is typically mediated by a covalent sonosensitiser-capsid bond, or by a non-covalent bond.

In one embodiment, the phage expresses at least one specific recognition element adapted to favour binding of the phage to target cells or to a virus, for example bacterial cells or tumour cells. In fact, phages can be engineered to express, on their capsid, at least one element capable of directing the phage towards a specific cell type. The phage preferably expresses at least one specific recognition element selected from an antibody, a receptor, a protein, a peptide and combinations thereof. In one embodiment, said specific recognition element is selected from: EGFR, HER2+, EGFRvIII, CD99, GD2, fibronectin, bacterial fimbriae and flagella and a peptide binding to the outer membrane of Gram-negative bacteria.

A second aspect of the present invention relates to a composition comprising the phage as described in detail above and excipients and/or additional substances and/or pharmaceutically accepted carriers.

According to a preferred embodiment of the of the invention, the composition is formulated for parenteral administration. In particular, the composition is formulated in liquid form, preferably in the form of a solution, emulsion or sterile suspension.

In one embodiment of the invention, the composition comprising the phage is formulated for enteral administration, preferably for oral administration. In particular, the composition is formulated in solid form, preferably in the form of pills, capsules, tablets, granular powder, hardshelled capsules, orally dissolving granules, sachets or lozenges.

In one embodiment, the composition is in lyophilised form, to be reconstituted so as to obtain a liquid formulation.

The phage of the present invention, thanks to the presence of at least one specific recognition element, is capable of selectively recognising some viruses or cell types, such as, for example, bacterial cells or tumour cells, and of binding them. Furthermore, thanks to the presence of a large number of sonosensitiser molecules, the phage enables the selective elimination of the cell types selected as the target. In fact, when irradiated with ultrasound, the sonosensitiser is capable of generating ROS, thus favouring the destruction of the cells to which the phage is bound.

Therefore, the phage can be used as a medicament, in particular in sonodynamic therapy (SDT) for the treatment of infections, preferably bacterial infections, or of tumours.

A third aspect of the present invention relates to the phage or to the composition as described above for use as a medicament, preferably in SDT.

The phage or the composition is preferably administered in association/in combination with ultrasound, also at a low intensity ($<0.03$ W/cm$^2$) preferably with an intensity greater than 0.05 W/cm$^2$.

A fourth aspect of the present invention relates to the phage or to the composition described above for use in the treatment or follow-up of a tumour, preferably a malignant tumour. In one embodiment, the tumour is a tumour with overexpression of at least one structure selected from: EGFR, HER2+, EGFRvIII, fibronectin, CD99 and GD2.

A further aspect of the present invention relates to the phage or to the composition described above for use in the treatment or prevention of an infection, preferably selected from a bacterial, viral or fungal infection, preferably a bacterial infection. In a preferred embodiment, the bacterial infection is caused by Gram-negative bacteria, such as, for example, *Pseudomonas, Escherichia, Klebsiella, Acinetobacter, Enterobacteriaceae, Salmonella, Shigella, Erwinia, Campylobacter, Helicobacter, Bordetella, Moraxella, Neisseria, Legionella, Listeria, Leptospira, Serpulina, Mycoplasma, Bacteroides, Yersinia, Vibrio*.

In one embodiment, the phage or the composition that comprises it is taken in association or in combination with other molecules, in particular with at least one antibiotic and/or with at least one antitumoural.

In one embodiment, the phage or the composition that comprises it is taken in association or in combination with a surgical treatment, preferably for the treatment of a malignant tumour, more preferably before or after an operation to remove the malignant tumour.

The advantages of the solution according to the present invention are to be sought in the conjugation of a sufficient number of sonosensitisers to the capsid of a bacteriophage (phage), at least 300 sonosensitisers/phage preferably at least 400, or at least 500, or at least 700, combined with an orthogonal protein/peptide display for selectively directing the phage to a specific cell type, so as also to enable SDT at low irradiation intensities, typical of instruments such as ultrasound scanners and physiotherapeutic sonotrodes. The advantages have been surprisingly obtained when at least 300 sonosensitisers have been conjugated to each phage, where the prior art showed that i) the conjugation of a phage with more than 400 photoreactive molecules reduced the effectiveness of the vector due to quenching effects (Li et al. 2010, cit.) and ii) high local sensitiser concentrations inactivated the phage itself (Costa et al. Viruses 2012, 4:1034-1074; doi:10.3390/v4071034; of Mascio et al. Biochim. Biophys. Acta 1989, 1007:151-157).

The Applicant has demonstrated that the efficiency of SDT in association with the phage of the present invention increases by at least two orders of magnitude compared to use of the same sensitiser not conjugated to the phage. The maintaining of a high selectivity, despite the high number of sonosensitiser molecules conjugated to the phages, indicates that the specific recognition elements (in orthogonal display) were not affected by decoration with the sonosensitisers. In other words, the conjugation of the sonosensitising molecules to the phage does not non compromise the specificity of the specific recognition elements. This represents a further advantage over prior art technologies, which provide for direct conjugation of sonosensitisers to the specific recognition elements, as it has been observed that they lose affinity for their targets when conjugated with a high number of effector molecules (Pèlegrin et al., 1991; van Dongen et al., 2004).

In fact, as shown in the examples, the killing of bacterial and tumour cells is mediated following sonodynamic irradiation of the sample, even when operating at low ultrasound intensities. The design scheme of the vector has the advantage of increasing the number of sensitisers delivered for each single binding event, thereby increasing the effectiveness of the SDT and making the application suitable for the use of physiotherapeutic sonicators or clinical ultrasound scanners.

A further aspect of the present invention relates to a method for the treatment or follow-up of a tumour, preferably a malignant tumour, or for the treatment or prevention of an infection. Said method comprises at least a step of administering an effective amount of a phage or of a composition that comprises it, as described above in detail, to an individual affected by a tumour or an infection.

The phage or the composition, is preferably administered in association/in combination with ultrasound, also at a low intensity (<0.3 W/cm$^2$), preferably with an intensity greater than 0.05 W/cm$^2$.

The infection is preferably selected from: a bacterial, viral or fungal infection, preferably a bacterial infection. In a preferred embodiment, the bacterial infection is caused by Gram-negative bacteria, such as, for example, *Pseudomonas, Escherichia, Klebsiella, Acinetobacter, Enterobacteriaceae, Salmonella, Shigella, Erwinia, Campylobacter, Helicobacter, Bordetella, Moraxella, Neisseria, Legionella, Listeria, Leptospira, Serpulina, Mycoplasma, Bacteroides, Yersinia* or *Vibrio*.

In one embodiment, the phage or the composition that comprises it is taken in association or in combination with other molecules, in particular antibiotics and/or antitumourals.

In one embodiment, the phage or the composition that comprises it is administered in association or in combination with a surgical treatment, preferably for the treatment of a malignant tumour, more preferably before or after an operation to remove the malignant tumour.

EXAMPLES

Example 1: Decoration of the Phages with Rose Bengal

A method of conjugating a sonosensitiser, namely, Rose Bengal, to the capside of the M13 phage is described here. The Rose Bengal (11.52 mg) was dissolved in DMSO (1 ml) and 1-ethyl-3-(3-dimethylaminopropyl) carbodiimide (6 mg) and N-hydroxy-succinimide (2 mg) were added for 5 hours under stirring in the dark at room temperature. One thus observes the activation of the carboxyl groups of Rose Bengal, which is necessary for the subsequent conjugation to the amino groups, prevalently of lysine, of the capsid proteins of the phage. 2.5 µl of the activated Rose Bengal solution were added to 50 µl of phage suspension in PBS and the mixture was kept under stirring overnight.

The conjugated phage was then separated from the free fraction of Rose Bengal by dialysis in PBS buffer. Three dialysis cycles were carried out, the first 2 for 4 hours and the third overnight, using 1 ml of solution to be dialysed and 200 ml of PBS.

Example 2: Calculation of the Phages Conjugated with Rose Bengal

Quantification of the phages was performed by reading the absorbance spectrum of the phages in UV and visible light, deriving the values for the wavelengths of 269 nm and 320 nm (FIG. 1*a*) and then applying the following formula:

$$virions/ml = \frac{(A_{360} - A_{720}) \cdot 6 \cdot 10^{16}}{opphagegenome}$$

In order to quantify the Rose Bengal conjugated to the phage ($C_{RB}$), the following formula was applied:

$$C_{RB} = \frac{(A_{536} - A_{720})}{\varepsilon_{555}^{RB}}$$

The phages decorated with Rose Bengal (FIG. 1*b*) were quantified by applying the formula:

$$virions/ml = \frac{\left(A_{269} - A_{360} - \left(\varepsilon_{360}^{RB} \cdot C_{RB}\right)\right) \cdot 6 \cdot 10^{16}}{opphagegenome}$$

Once the concentrations of the Rose Bengal ($C_{RB}$) and of the phages (virions/ml) are known, the Rose Bengal molecule/phage ratio is derived. The decorated phages were classified for the subsequent experiments: a) decorated with fewer than 300 sonosensitisers; b) from 300 to 700 sonosensitisers; and c) more than 700 sonosensitisers.

Example 3: Decoration of Phages with Chlorin e6

Chlorin e6 (6 mg) was dissolved in DMSO (1 ml) and 1-ethyl-3-(3-dimethylaminopropyl) carbodiimide (6 mg) and N-hydroxy-succinimide (5 mg) were added for 5 hours under stirring in the dark at room temperature. One thus observes the activation of the carboxyl groups of Chlorin e6, which is necessary for the subsequent conjugation to the amino groups, prevalently of lysine, of the capsid proteins of the phage. 2.5 µl of the activated Chlorin e6 solution were added to 50 µl of phage suspension in PBS and the mixture was kept under stirring overnight.

The conjugated phage was then separated from the free fraction of Chlorin e6 by dialysis in PBS buffer. Three dialysis cycles were carried out, the first 2 for 4 hours and the third overnight, using 1 ml of solution to be dialysed and 200 ml of PBS.

Once the concentrations of Chlorin e6 ($C_{Ce6}$), obtained by reading the absorbance of Chlorin e6 at 663 nanometres, and of the phages (virions/ml) are known, the Chlorin e6 molecule/phage ratio is derived by using equations analogous to those presented in Example 2, and is equal to 1180/1.

Example 4: Cytotoxicity after SDT in the Presence of Phages Conjugated to Chlorin e6

Figure 2:
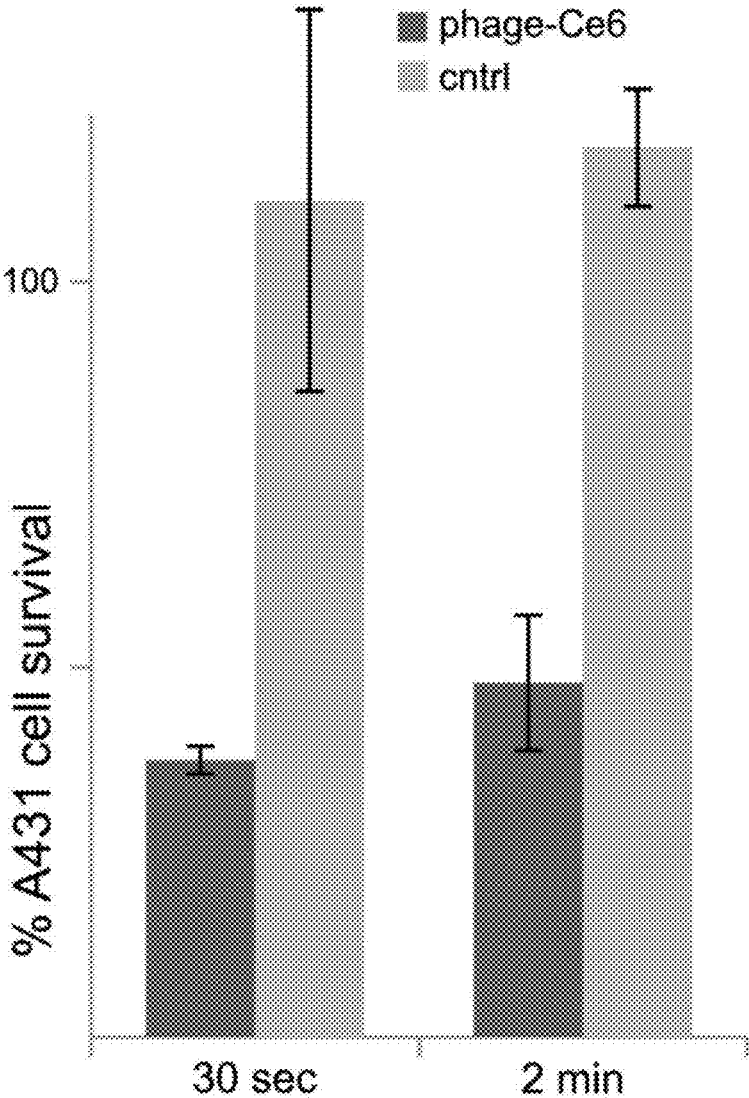
FIG. 2 shows the cytotoxic effect of phages conjugated with chlorin e6 (Ce6) on an epidermoid carcinoma A431 cell line in the presence of ultrasound radiation.

M13 phages conjugated with chlorin e6 (Ce6), redirected orthogonally for recognition of the epidermoidal carcinoma A431 line which overexpresses the receptor EGFR, were incubated for 45 min with the cell line and then exposed to an ultrasound source at a medium-low intensity (1 W/cm2), in a dark environment for different times. The data indicate the percentage of viable cells compared to the same samples kept in the dark without sonication. A cytotoxic effect was observed only with the phages conjugated to Ce6 in the presence of ultrasound irradiation (phage-Ce6). In the absence of decorated phages (cntrl), no cytotoxicity effects were found (FIG. 2).

Example 5: Decoration of Phages with Protoporphyirin IX

Protoporphyirin IX (6 mg) was dissolved in DMSO (1 ml) and 1-ethyl-3-(3-dimethylaminopropyl) carbodiimide (6 mg) and N-hydroxy-succinimide (2 mg) were added for 5 hours under stirring in the dark at room temperature. One thus observes the activation of the carboxyl groups of Protoporphyirin IX, which is necessary for the subsequent conjugation to the amino groups, prevalently of lysine, of the capsid proteins of the phage. 2.5 µl of the solution of activated Protoporphyirin IX was added to 50 µl of phage suspension in PBS and the mixture was kept under stirring overnight. The conjugated phage was then separated from the free fraction of Protoporphyirin IX by dialysis: 3 dialysis cycles, the first 2 for 4 hours in sodium carbonate buffer 0.1 M, pH 9 and the third overnight in PBS, using 1 ml of solution to be dialysed and 200 ml of buffer.

Once the concentrations of Protoporphyirin IX ($C_{PPIX}$), obtained by reading the absorbance of the Protoporphyirin IX at 408 nanometres, and of the phages (virions/ml) are known, the Protoporphyirin IX molecule/phage ratio is derived by using equations analogous to those presented in Example 2, and is equal to 468/1.

Example 6: Decoration of the Phages with Cyanine IR-806

The method of conjugating a sonosensitiser, namely, Cyanine IR-806, to the capsid of the M13 phage is described here. The Cyanine IR-806 (7.3 mg) was dissolved in DMSO (1 ml).

2.5 µl of the solution of Cyanine IR-806 dissolved in DMSO were added to 50 µl of phage suspension in sodium carbonate buffer 0.1 M, pH 9 and the mixture was kept under stirring overnight. One thus observes a reaction of conjugation of the Cyanine IR-806 to the nucleophilic groups, prevalently of lysine, of the capsid proteins of the phage through a nucleophilic substitution reaction.

The conjugated phage was then separated from the free fraction of Cyanine IR-806 by means of 5 dialysis cycles, the first 3 dialysis cycles for 4 hours in sodium carbonate buffer 0.1 M, pH 9, the fourth cycle of dialysis for 48 hours in sodium carbonate buffer 0.1 M, pH 9 and the fifth cycle of dialysis overnight in PBS, again using 1 ml of solution to be dialysed and 200 ml of buffer.

Once the concentrations of Cyanine IR-806 ($C_{IR806}$), obtained by reading the absorbance of the Cyanine IR-806 at 686 nanometres, and of the phages (virions/ml) are known, the Cyanine IR-806/phage molecule ratio is derived by using equations analogous to those presented in Example 2, and is equal to 870.

Figure 3:
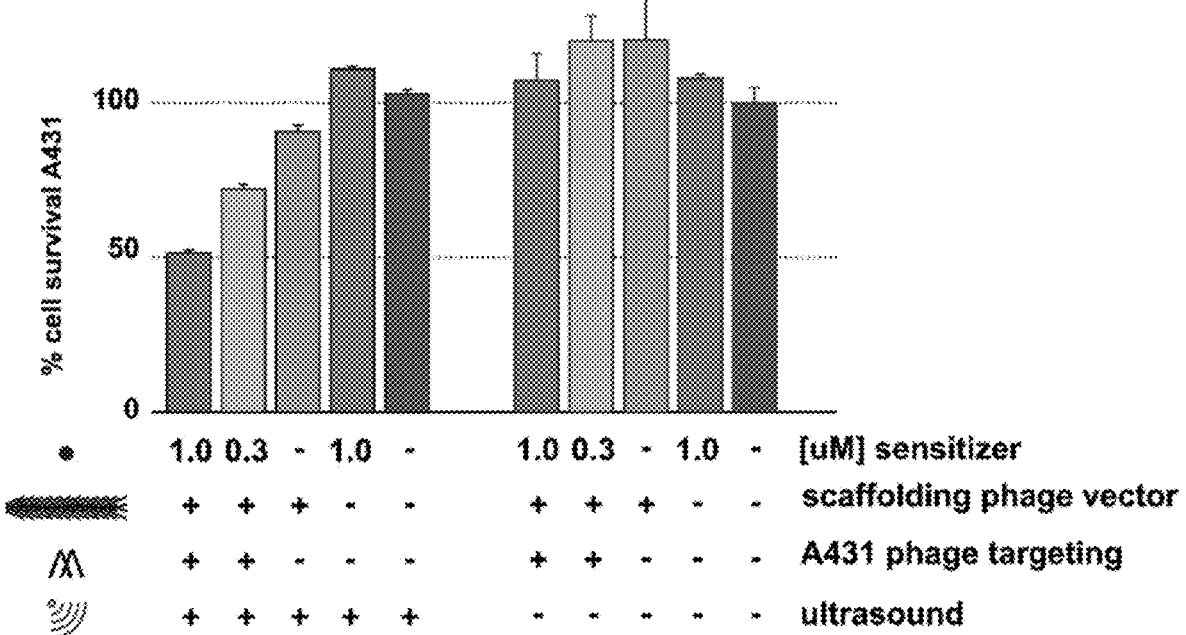
FIG. 3 shows the cytotoxic effect of phages conjugated with Rose Bengal (RB) on the epidermoid carcinoma A431 cell line in the presence of ultrasound irradiation.

Example 7: Cytotoxicity after SDT in the Presence of Phages Conjugated to Rose Bengal M13 phages conjugated to Rose Bengal (RB) were redirected orthogonally for recognition of an epidermoidal carcinoma line which overexpresses the receptor EGFR (A431), by fusion of a peptide for binding to EGFR onto the protein pill of the phage. The phages were incubated for 45 min with the cell line and then exposed to an ultrasound source at a low intensity (<0.3 W/cm$^2$) in a dark environment for 30 minutes. The negative controls were kept in the dark without sonication. A dose-dependent cytotoxic effect was observed only with the phages conjugated to RB in the presence of ultrasound irradiation. In the absence of decorated phages, no cytotoxicity effects were found (FIG. 3).

Figure 4:
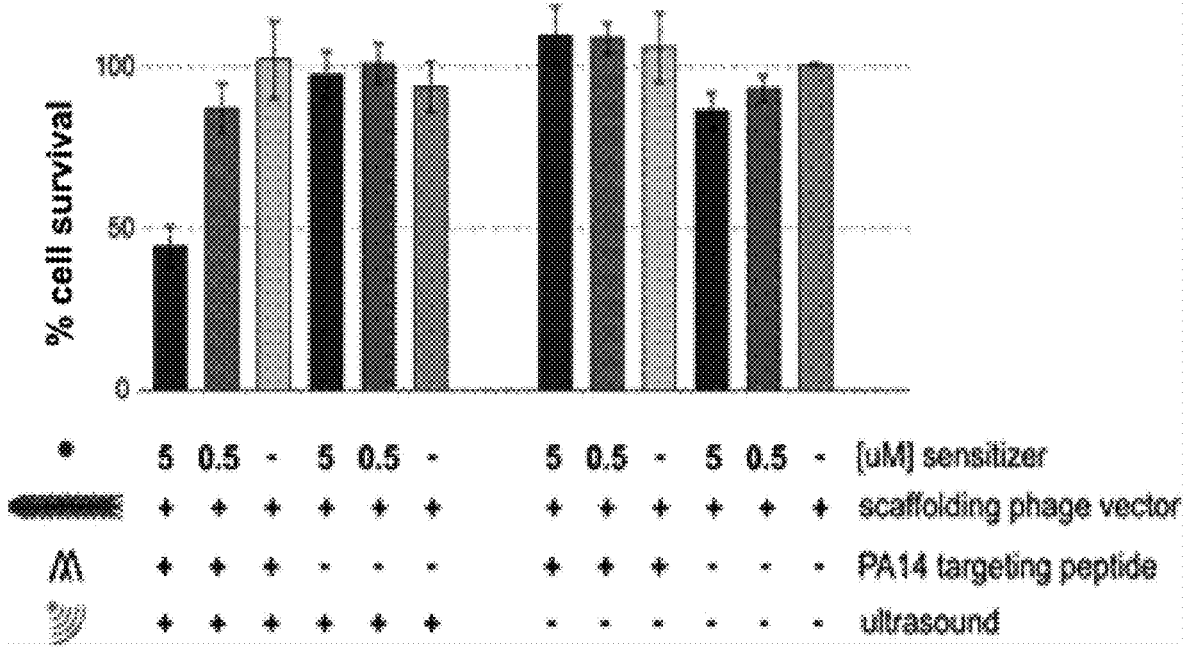
FIG. 4 shows the antimicrobial effect of phages conjugated with RB on the opportunistic pathogenic bacterium *Pseudomonas aeuriginosa* in the presence of ultrasound irradiation (% cell survival=% viable cells).

Example 8: Antimicrobial Effectiveness of SDT in the Presence of Phages Conjugated To Rose Bengal Conjugated Rose Bengal phages were redirected for recognition of Gram-negative bacteria, including the opportunist pathogen *Pseudomonas aeruginosa*, strain PA14. The bacteria were incubated with the phages conjugated to RB for 30 minutes and subsequently irradiated with ultrasound in a dark environment for 30 minutes. The negative controls were kept in the dark without sonication. A dose-dependent antimicrobial effect was observed only with the phages conjugated to RB in the presence of ultrasound irradiation. In the absence of decorated phages, no antimicrobial effects were found (FIG. 4).

Example 9: Efficiency of Targeting and Cytotoxic Effect with Low-power Sonication The experiment had the objective of testing the minimum power necessary to obtain the desired cytotoxic effect.

Data from the literature (Li et al. 2010) show that the overexposure of more than 400 marker units per phage leads to a diminished performance of the phage itself.

Rose Bengal phages were conjugated with fewer than 300 sonosensitisers, from 300 to 700 sonosensitisers or more than 700 sonosensitisers and were redirected for recognition of Gram-negative bacteria or for recognition of an epidermoidal carcinoma line which overexpresses the receptor EGFR (A431).

Figure 5:
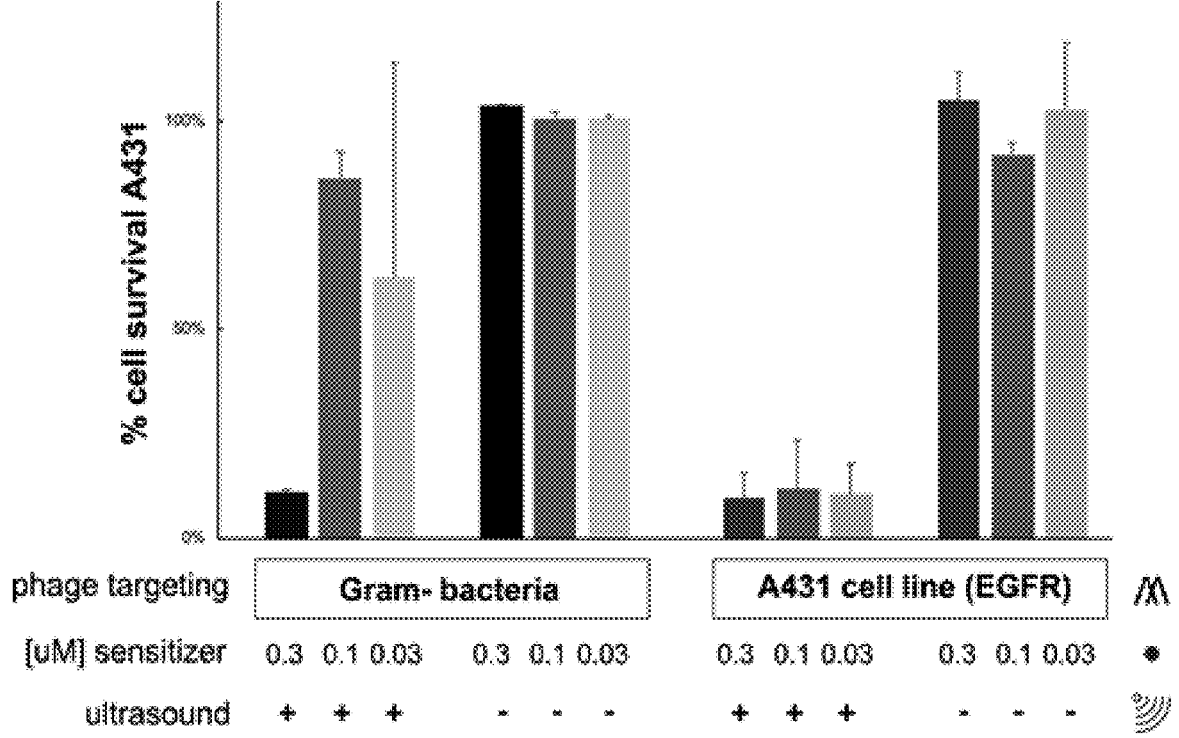
FIG. 5 shows the phage-mediated SDT selectivity. Phages conjugated with RB (>700 sensitisers/phage), designed to expose a peptide binding EGFR onto the minor capsid protein (pIII), promote the sonodynamic elimination of the epidermoid carcinoma A431 cell line already at an RB concentration of 30 nM. At the same concentrations of RB, the phages directed against Gram-negative bacteria are not able to mediate the SDT killing of the A431 cell line.

The results are shown in table 1 and in FIG. 5.

9 | 10

TABLE 1 phage-mediated SDT (% dead cells); sonication intensity <0.3 W/cm².

| target | Gram -Bacteria | | Cell line A431 | | | |
|---|---|---|---|---|---|---|
| Sonosensitiser [μM] | [5.0] | [0.5] | [1.0] | [0.3] | [0.1] | [0.03] |
| sonosensitiser/phage | | | | | | |
| <300 | 0 | 0 | 0 | 0 | 0 | 0 |
| 300-700 | NA | NA | 48.5 ± 0.9 | 27.9 ± 1.4 | NA | NA |
| >700 | 55.9 ± 6.4 | 13.3 ± 7.7 | NA | 90.8 ± 6.4 | 88.9 ± 11.9 | 90 ± 8.2 |

Vectors decorated with fewer than 300 sonosensitisers per phage demonstrated to be very effective in their ability to kill cells selectively with photodynamic therapy (PDT) (data not shown), thus indicating effective targeting, but they did not achieve any cytotoxic effect with low-power sonodynamic irradiation (Table 1).

Surprisingly, the targeting vectors conjugated with 500 sensitisers/phage demonstrated to be more effective for SDT on an epidermoid carcinoma cell line with overexpression of EGFR (cell line A431 Table 1 and FIG. 3). Moreover, a further increase in the number of sensitisers (>700) demonstrated to be effective also for SDT against pathogenic bacteria (Gram-negative bacteria Table 1 and FIG. 5). Furthermore, these heavily conjugated vectors also improved the effectiveness of SDT on the cancer cell line, thus significantly reducing the concentration of RB necessary in order to observe a cytotoxic effect compared to less decorated phages. In particular, the vectors maintained an excellent selectivity. The phage vectors directed against the membrane of the Gram-negative bacteria (Table 1 and FIG. 5) did not show cytotoxic effects at lower concentrations of RB, in which the phage vectors optimised for EGFR demonstrated to be efficient. The maintaining of a high selectivity, despite the high number of RB molecules conjugated to the phages, indicates that the directing molecules (in orthogonal display) were not affected by decoration with RB. This represents a further advantage over technologies of the prior art, which envisage the direct conjugation of sonosensitisers to directing molecules, as it has been observed that the latter lose affinity for their targets when conjugated with a high number of effector molecules (Pèlegrin et al., 1991; van Dongen et al., 2004).

The invention claimed is:

1. A method for treating a tumour or an infection, said method comprising administering to a subject a phage expressing at least one specific recognition element, said specific recognition element being conjugated with at least 300 molecules of a sonosensitiser or a composition comprising the phage and excipients and/or additional substances and/or pharmaceutically accepted carriers wherein the infection is selected from a bacterial, viral or fungal infection, and wherein the phage is administered in association or in combination with ultrasound.

2. The method according to claim 1, wherein said tumor is a malignant tumor and said infection is a bacterial infection.

3. The method according to claim 2, wherein the tumor is a tumor with overexpression of at least one structure selected from: EGFR, HER2⁺, EGFRvIII, fibronectin, CD99, GD2 and combinations thereof.

4. The method according to claim 1, wherein the phage is administered in association or in combination with at least one antitumoral, or in association with at least one antibiotic.

5. The method according to claim 1, wherein the phage is administered in association or in combination with a treatment of a malignant tumor.

6. The method according to claim 1, wherein the phage is administered in before or after an operation to remove the malignant tumor.

7. The method according to claim 1, wherein the sonosensitiser is selected from: Bacteriochlorin, Phthalocyanines, Pheophorbide A and B, Bacteriopheophorbide, Naphthalocyanine, BODIPY stains, Anthracycline, Tetracycline, Fluoroquinolones, Phenothiazine, Perylene, Perylenequinone, Curcumin, Quinones, Anthraquinones, Fullerenes, Endohedral Metallofullerenes, Acridines, Isoquinole alkaloids, Xanthenes, Porphyrins, Chlorins and Cyanine.

8. The method according to claim 1, wherein the sonosensitiser is selected from: a xanthen, a porfirin, a chlorin, a cyanine, and combinations thereof.

9. The method according to claim 1, wherein the xanthen is selected from rose bengal, eosin, erythrosin B, fluorescein and rhodamine; the porphyirin is selected from protoporphyirin IX, hematoporphyirin, porfimer sodium and ATX-70; the chlorin is selected from chlorin e6, temoporfin and verteporfin; the cyanine is selected from cyanine IR-806, indocyanine green and cyanine IR-780, and combinations thereof.

10. The method according to claim 1, wherein said phage is conjugated with at least 400 sonosensitiser molecules.

11. The method according to claim 1, wherein the phage is selected from the M13 phage, fd phage, Ff phage, T4 and MS2 phage.

12. The method according to claim 1, wherein said specific recognition element is selected from: an antibody, a receptor, a protein, a peptide and combinations thereof.

13. The method according to claim 1, wherein said specific recognition element is selected from: EGFR, HER2⁺, EGFRvIII, CD99, GD2, fibronectin, bacterial fimbriae and flagella and a peptide binding to the outer membrane of Gram-negative bacteria.

14. The method according to claim 1, wherein said phage is conjugated with at least 500 sonosensitizer molecules.

15. The method according to claim 1, wherein said phage is conjugated with at least 700 sonosensitizer molecules.

16. The method according to claim 1, wherein the phage is M13 phage.

* * * * *